(12) United States Patent
Peterman et al.

(10) Patent No.: US 8,585,881 B2
(45) Date of Patent: Nov. 19, 2013

(54) LOCALIZED CHEMICAL MICROGRADIENTS

(75) Inventors: Mark C. Peterman, Jackson, WY (US); David M. Bloom, Jackson, WY (US)

(73) Assignee: Onda Via, Inc., Hayward, CA (US)

(*) Notice: Subject to any disclaimer, the term of this patent is extended or adjusted under 35 U.S.C. 154(b) by 2004 days.

(21) Appl. No.: 10/711,327

(22) Filed: Sep. 10, 2004

(65) Prior Publication Data

US 2006/0054502 A1 Mar. 16, 2006

(51) Int. Cl.
*B01D 57/02* (2006.01)
(52) U.S. Cl.
USPC .......................................................... 204/450
(58) Field of Classification Search
USPC .................... 204/450; 435/461, 470
See application file for complete search history.

(56) References Cited

U.S. PATENT DOCUMENTS

| | | | | |
|---|---|---|---|---|
| 5,603,351 | A * | 2/1997 | Cherukuri et al. | 506/33 |
| 2003/0015425 | A1 * | 1/2003 | Bohm et al. | 204/453 |
| 2003/0032946 | A1 | 2/2003 | Fishman | |
| 2006/0121464 | A1 * | 6/2006 | Jespersen et al. | 435/6 |

OTHER PUBLICATIONS

Kathryn G. Klemic et al., "Micromolded PDMS planar electrode . . . ," Biosensors and Bioelectronics v. 17, p. 597, 2002.
A. Tixier, et al., "Catching and attaching cells using an array of microholes," IEEE-EMBS Conference on Microtechnologies in Medicine & Biology, Poster 106, Oct. 12, 2000.
Mark C. Peterman et al., "Fluid Flow Past an Aperture in a Microfluidic Channel," Analytical Chemistry v. 76, p. 1850, Apr. 1, 2004.
Mark C. Peterman et al., "Localized chemical release from an artificial synapse chip," PNAS v. 101, p. 9951, Jul. 6, 2004.

* cited by examiner

*Primary Examiner* — Jennifer Michener
*Assistant Examiner* — Dustin Q Dam
(74) *Attorney, Agent, or Firm* — NUPAT, LLC; Morrison Ulman

(57) ABSTRACT

A device for creating microgradients in solution is disclosed. The device contains a microfluidic channel with openings at each end and two or more small apertures to a bath. Electrodes are placed in the openings at either end of the channel and an electrical power supply is connected to the electrodes. Several distinct current paths exist from one end of the channel to the other. For example current may flow from one electrode, through a portion of the channel, through an aperture into the bath, back through another aperture into the channel, and along another portion of the channel to the other electrode. Current flows along all possible connected paths when an electric field is applied along the channel and induces fluid flow into and out of the apertures in the channel. Fluid flow through the apertures results in the formation of microgradients in solution near the microfluidic channel device.

6 Claims, 9 Drawing Sheets

LOCALIZED CHEMICAL MICROGRADIENTS

BACKGROUND

The field of the invention generally relates to microfluidic structures and methods of using them to interface measurement devices to living cells. More specifically the field of the invention relates to the creation and control of chemical gradients over length scales commensurate with the size of biological cells.

Much of modern biological research is concerned with the study of living cells. Countless investigations of cells have greatly increased our understanding of biological processes and have led to improved treatment of disease and reduced suffering of ill patients.

Many biological advances come from the application of known research techniques to cells or biological molecules which have not been studied before. However, the greatest leaps in understanding often occur when new research tools are invented. Nearly 400 years ago, for example, Anton van Leeuwenhoek of Holland pioneered the use of microscopes in biology. He was the first to see and describe bacteria, yeast plants, the teeming life in a drop of water, and the circulation of blood corpuscles in capillaries.

Today researchers not only look at cells, but probe, excite, influence and control them with a variety of methods, always with the goal of understanding more about how cells work and interact with their environment. Often glass capillary tubes, drawn out to have very sharp tips, are used to probe cell behavior and modify a cell's local environment.

Conventional research techniques include using tubular glass micropipettes with tips as small as one micron in diameter. Researchers use micromanipulators to position micropipette tips near cells under a microscope. For "patch clamping" experiments a tip is sealed over a patch of the cell membrane. For experiments on "chemotaxis", or the movement of cells along gradients of concentration of dissolved substances, a tip is placed very close to the cell and a solution is squirted out.

Micropipettes are used in many other types of biological experiment, but fundamentally the tip of the pipette is always brought very close to, or in contact with, a cell for the purpose of modifying or sampling the cell's local environment. A solution may be squirted out near the cell in an attempt to provoke a reaction from it. Alternatively a small volume of solution from the cell's immediate surroundings may be sucked into the end of the pipette for analysis.

One of the limitations of micropipettes is that they are difficult to manipulate due to their large size in relation to the cell being measured. A highly trained technician is required to use them effectively. It is also generally not feasible to operate more than one micropipette at a time during an experiment. Therefore only single cells, rather than organized collections of cells are studied.

According to Klemic et al. in Biosensors and Bioelectronics (v. 17, p. 597, 2002) "there is tremendous interest in improving the throughput and 'ease of use' of the patch clamp method, primarily to facilitate drug screening in the pharmaceutical industry . . . " Further, the conventional "method is not practical for high-throughput screening because it requires a skilled operator to manually manipulate the glass pipette onto the cell."

Micropipettes are used in chemotaxis experiments to show how cells may be attracted to concentration gradients of certain substances dissolved in solution. Using microscopes, researchers have made movies of cells chasing a micropipette tip whenever a solution is ejected from the tip. It would be highly desirable, however, to be able to characterize and quantify the concentration gradient that influences the cell or even to create a concentration gradient around a cell that is fixed in position.

Overall, a better interface to living cells is needed. A long-felt need for a cell interface exists in the art of cell studies as evidenced by the popularity of micropipettes in the face of their limited capabilities.

Structures that could create controllable, highly localized concentration gradients in the immediate vicinity of cells would be useful in myriad biological experiments. Structures that could organize cells into ordered groups would be advantageous for parallelizing cell investigations instead of performing experiments one cell at a time. Structures that could deliver reagents to the immediate vicinity of cells would be useful for drug screening. The present lack of structures with these capabilities would make the invention of a new cell interface device all the more surprising.

SUMMARY

An aspect of the invention provides a device for creating microgradients in solution. The device comprises a microfluidic channel with openings at each end and two or more small apertures to a bath. Electrodes are placed in the openings at either end of the channel and an electrical power supply is connected to the electrodes. Several distinct current paths exist from one end of the channel to the other. For example, current may flow from one electrode, through a portion of the channel, through an aperture into the bath, back through another aperture into the channel, and along another portion of the channel to the other electrode. Current flows along all possible connected paths when an electric field is applied along the channel and induces fluid flow into and out of the apertures in the channel. Fluid flow through the apertures results in the formation of microgradients in solution near the microfluidic channel device.

BRIEF DESCRIPTION OF THE DRAWINGS

The drawings are heuristic for clarity. The foregoing and other features, aspects and advantages of the invention will become better understood with regard to the following descriptions, appended claims and accompanying drawings in which:

DETAILED DESCRIPTION

Figure 1:
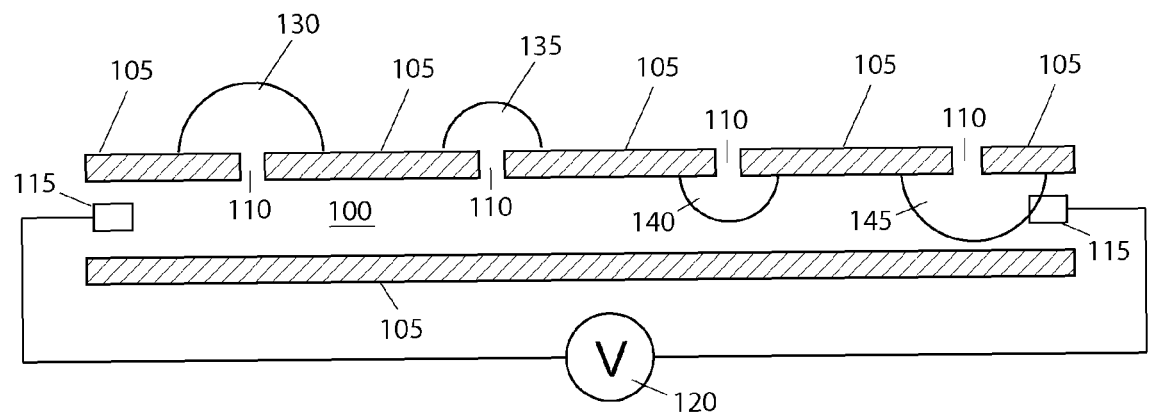
FIG. 1 is a cut-away, side view of a microfluidic channel device.

According to an aspect of the invention a device that releases chemical compounds in small volumes at multiple, well-defined, locations is disclosed. The device is a powerful tool for clinical therapeutics and biological research. For example, implantable drug delivery devices and neurotransmitter-based neural prostheses both require the controlled release of chemical compounds. Further, basic research requiring control over chemical gradients, such as studies of cell microenvironments, stem-cell niches, metaplasia or chemotaxis, would benefit from a general chemical release device.

A basic component of a device according to an aspect of the invention is a closed channel a few microns across and a few hundred microns or even millimeters long. It is also possible, and sometimes desirable, to make channels as narrow as 100 nanometers across. Many microfluidic devices incorporate such channels which are sometimes also referred to as "microchannels". However, unlike a conventional channel, a channel according to an aspect of the invention comprises two or more small apertures in one or more of the walls of the channel. The apertures connect the channel to a fluid reservoir or bath in which a sample solution may be located. According to an aspect of the invention, a single channel may have multiple apertures and a single device may have many channels.

It is well known that when a polar solution such as water is loaded into a microchannel a charged double layer is formed at the walls. In the case of water —OH groups bind to the channel walls while positive ions remain free in solution. The fixed negative charge on the channel wall causes positive ions to migrate toward the wall. These two layers of charge are the constituents of the well known electric double layer.

When an electric field is applied along the channel mobile positive ions are driven down it. The flow of ions drags the entire solution down the channel because of the high polarity of water. In other words, application of an electric field to a microchannel filled with a polar solution causes the solution to flow. The velocity of the flow is proportional to the electric field strength. This phenomenon is known as electroosmosis or electroosmotic flow, sometimes abbreviated EOF. It is simple to apply and control which explains its frequent use in microfluidics.

If small apertures are present in the wall of a microchannel, it is still a simple matter to induce electroosmotic flow by applying an electric field down the length of the channel. If there is only one aperture the electric field is hardly disturbed compared to the case when the channel has no apertures in its walls.

According to an aspect of the invention, however, when multiple apertures are provided in a microchannel several distinct current paths exist from one end of the channel to the other and current flows along all of these paths when an electric field is applied along the channel. This is a key aspect of the invention.

For example, in a channel containing two apertures to a bath, there is a current path down the longitudinal axis of the channel from one end to the other. However, there is also a current path from one end of the channel, up through one aperture into the bath, down through the other aperture back into the channel, and along the channel to the other end. Consequently there is an electric field out one aperture and back in the other. These fields lead to fluid flow out of the channel at one aperture and into the channel at the other aperture. Fluid flow into and out of a bath, connected to a microchannel by apertures in the walls of the microchannel, is a remarkable aspect of the invention.

According to an aspect of the invention cells are cultured near an aperture of a multi-aperture microchannel. The cells are bathed in solution ejected from the channel by the mechanism just described. The solution may contain, as an example, a putative cancer drug and the cultured cells may be a mixture of cancerous and non-cancerous cells. If the drug is observed to destroy only the cancerous cells it is an excellent candidate for cancer therapy. With hundreds of apertures and channels in one device a variety of concentrations or compounds can be tested simultaneously. Parallel testing of multiple compounds dramatically reduces the time and expense of drug trials.

According to an aspect of the invention a microchannel with multiple apertures connecting the inside of the channel to a bath may be used as part of an array of biological cells each with a controlled microenvironment. The microchannel device causes chemical solutions to flow through each aperture in the channel simultaneously. Further, appropriate adhesion proteins may be patterned near each aperture for combinatorial studies or cell signaling experiments.

According to an aspect of the invention, in a multi-aperture microfluidic channel device with an electric field applied along the channel, half of the apertures will eject fluid into the bath while fluid will be withdrawn from the bath into the channel through the remaining apertures. However, according to another aspect of the invention it is possible to make a device in which fluid ejection from the channel into the bath occurs at all apertures. Alternatively, it is also an aspect of the invention that a device may be constructed in which fluid withdrawal from the bath into the channel through each of several apertures occurs simultaneously.

According to an aspect of the invention, pressure, in addition to an electric field, may be applied along a microchannel. In this case, fluid ejection from the channel into the bath will occur at more than half of, or as many as all of, the apertures. According to an aspect of the invention, the simultaneous ejection of fluid results in the formation of a chemical concentration gradient above the apertures along the channel. If biological cells are cultured near each aperture each cell will be exposed to its own separate chemical microenvironment.

According to further aspects of the invention a microchannel may have any number of apertures greater than one. The apertures may be in any of the walls of the channel, but all of them, or at least groups of two or more of them, must connect to a common bath. An aspect of the invention includes a channel in which some apertures connect the channel to a first bath while others connect the channel to a second bath and so on up to any number of baths.

According to an aspect of the invention microchannels may be made of any material that supports electroosmotic flow and although they are often drawn schematically as straight channels they may in fact incorporate bends or other shapes. A device according to the invention may incorporate any number of channels, some or all of which may be individually controlled. Each channel requires two electrodes to control fluid flow and these electrodes may be created during the fabrication process or inserted into the ends of the channel during use.

Multi-aperture microfluidic channel devices have yet further applications according to an aspect of the invention. The fluid ejection and fluid withdrawal features described above may be used to position biological cells on or within apertures in the channel. When an electric field is applied along channel containing an array of apertures, half of the apertures eject fluid to the bath while the others withdraw fluid from the bath. If there is only one aperture or if all but one aperture is clogged, for example by a biological cell, no fluid flow between the channel and the bath occurs.

According to an aspect of the invention cells may be introduced to a bath that is connected to a channel by multiple apertures. Alternatively cells may be introduced to a channel connected to a bath by multiple apertures. When an electric field is applied along the channel fluid flows out of some apertures and in through others. As a cell nears an aperture it will be sucked partially into the aperture by fluid flow. When the cell becomes seated in the aperture it will seal off current flow. The seal formed may or may not be as perfect or tight as a gigaohm seal or "gigaseal" as commonly known in the art of patch clamping. However, the seal provides a self-regulating mechanism for loading cells into the apertures in a channel. As soon as a cell occupies an aperture the electric field drops to zero and fluid flow through the aperture stops resulting in a precisely positioned cell. Cells continue to be sucked into the apertures in the device until cells are trapped in all but one aperture of a channel. Furthermore once cells are in position the portion of the cell that is exposed to the channel can be incubated with a precisely controlled solution.

According to further aspects of the invention the technique of sucking cells into apertures may be extended to a method of sorting cells. For example, since the cells sit at precisely known positions defined by the location of the apertures, their reaction to gradients of chemicals in solution may be recorded. A channel may also be constructed with apertures of different sizes. Cells smaller than the size of an aperture will pass through it while larger cells get stuck.

Turning now to the figures, FIG. 1 is a cut-away, side view of a microfluidic channel device according to an aspect of the invention. The channel 100 is a long, hollow structure that is closed except for openings at each end and small apertures 110 in one or more of the walls 105. The dimensions of the channel may be approximately 1 to 100 microns across and 100 to 10,000 microns long. Electrodes 115 are placed in or near the openings at either end of the channel. The electrodes are connected electrically to an electrical power supply or voltage source 120.

During operation of the microfluidic channel device, channel 100 is filled with a polar fluid such as water and an external fluid bath is placed in contact with apertures 110 so that fluid is free to flow from the channel through an aperture and into the bath and vice versa. The bath is isolated from the ends of the channel so that all fluid flow between the channel and the bath must be via apertures 110. FIG. 1 shows four apertures 110; however, a device according to an aspect of the invention may incorporate two or more apertures up to any number of apertures.

Figure 2:
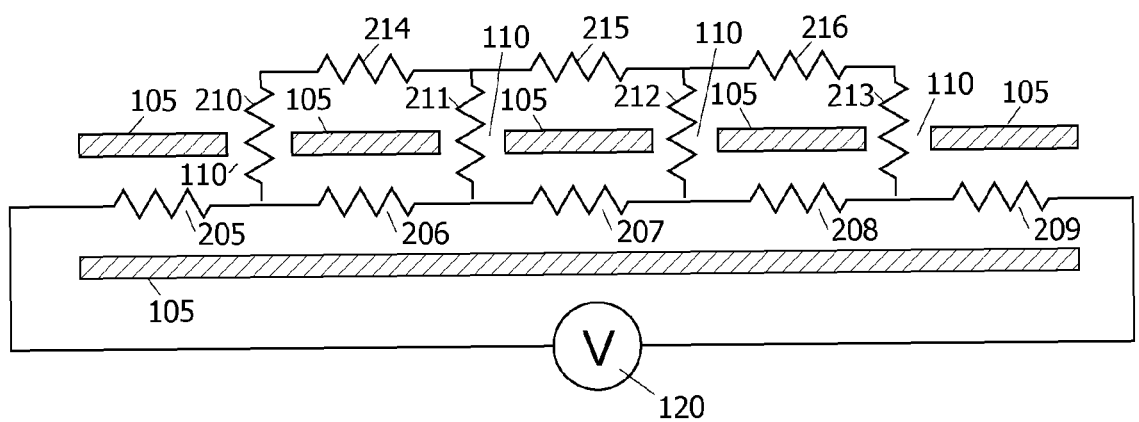
FIG. 2 is a simplified, electrical schematic diagram of the current paths in the device of FIG. 1.

Power supply 120 and electrodes 115 to which it is connected create an electric field along the length of channel 100. There are many possible current paths between electrodes 115 including straight down the channel or through an aperture into the external bath and back through another aperture. FIG. 2 is a simplified, electrical schematic diagram of the current paths in the device of FIG. 1.

In FIG. 2 resistors 205, 206, 207, 208, 209, 210, 211, 212, 213, 214, 215 and 216 represent electrical current paths between electrodes 115 of FIG. 1. For example one current path includes resistors 205, 206, 207, 208 and 209 while another includes resistors 205, 210, 214, 211, 207, 208 and 209. Put another way, the microfluidic channel device of FIG. 1 may be represented electrically by the resistor network of FIG. 2.

When the microchannel device of FIG. 1 is filled with a polar fluid such as water, placed in contact with an external reservoir as described above, and a voltage is applied by power supply 120, fluid will flow from one end of channel 100 to the other by electroosmotic flow. However, fluid will also be ejected from some of apertures 110 into the bath and withdrawn from others of apertures 110 back into the channel. In FIG. 1 the ejection of fluid into the bath is represented schematically by fluid boundaries 130 and 135. The withdrawal of fluid from the bath into the channel is represented schematically by fluid boundaries 140 and 145.

Fluid boundary 130 is larger than boundary 135, and boundary 145 is larger than boundary 140. This is a characteristic of the device which leads to a gradient in the amount of fluid ejected from one end of the device to the other. However, the schematic, semicircular shape of boundaries 130, 135, 140 and 145 is only a guide to visualizing the difference in the amount of fluid inflow or outflow through apertures 110. The fluid is not necessarily ejected or withdrawn along semicircular fronts. Diffusion, for example, may change the pattern of an outgoing or incoming fluid stream.

Figure 3:
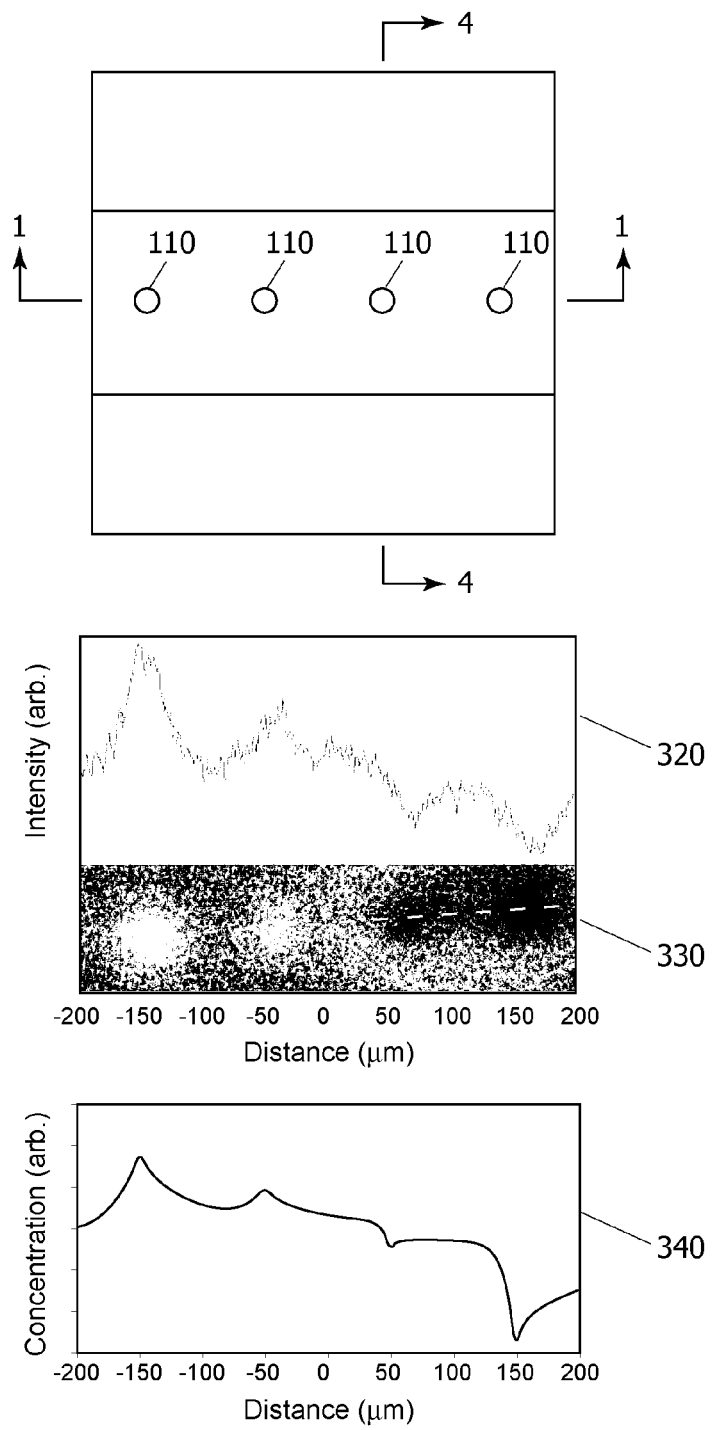
FIG. 3 shows experimental data and theoretical simulations of concentration gradients in solution created with a device such as that illustrated in FIG. 1.

FIG. 3 shows experimental data and theoretical simulations of concentration gradients in solution created with a device such as that illustrated in FIG. 1. Device 310 is a microfluidic channel device according to an aspect of the invention shown from the top. Line 1-1 indicates the section of device 310 that is shown in FIG. 1.

Panels 320 and 330 show experimental results obtained with device 310. In the experiment fluorescein dye was placed in solution and introduced into the microfluidic channel device. Panel 330 is a fluorescence photograph of part of the top of the device. Brighter areas indicate regions of greater fluorescein concentration while darker areas indicate regions of lesser fluorescein concentration. There are four distinct spots in the image corresponding to apertures 110 in device 310. The white dashed line in panel 330 is the location of the intensity line scan shown in panel 320.

Panel 320 shows that a microfluidic channel device according to an aspect of the invention causes a concentration gradient of fluorescein to be formed in the bath immediately adjacent to apertures 110.

Panel 340 shows the results of numerical modeling of the microfluidic channel device. The computed concentration gradient shown in panel 340 is quite similar to the experimentally measured gradient presented in panel 320.

Figure 4A:
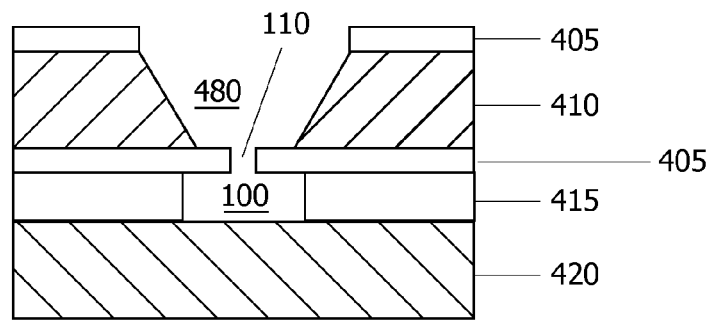
FIG. 4A, FIG. 4B and FIG. 4C show alternative material structures for realizing the microfluidic channel device of FIG. 1.
Figure 4B:
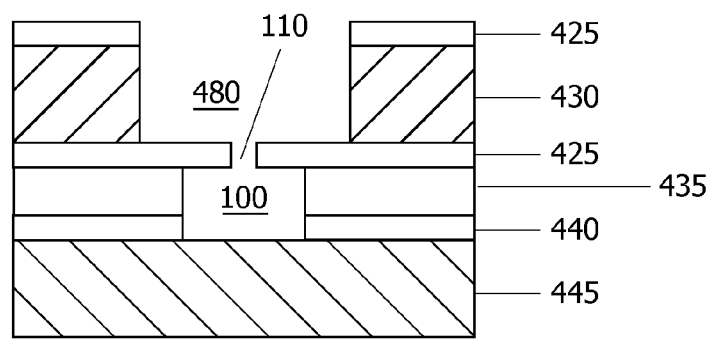
Figure 4C:
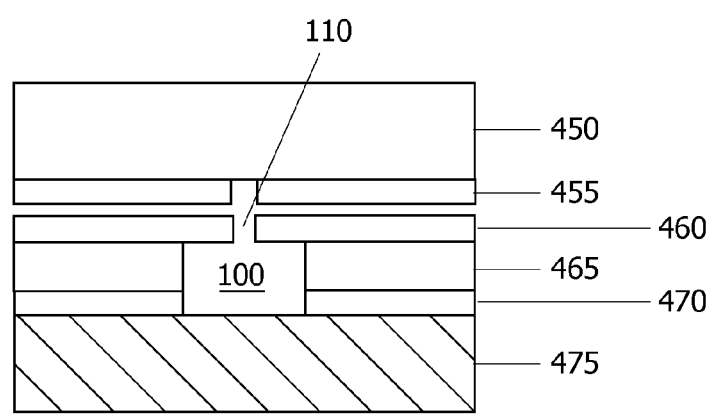

FIGS. 4A, 4B and 4C show alternative material structures for realizing the microfluidic channel device of FIG. 1. The structures depicted in FIGS. 4A and 4B are fabricated starting from silicon wafers while the structure depicted in FIG. 4C starts with a glass wafer but has as its final result a flexible structure. Although the fabrication methods described below in reference to FIGS. 4A, 4B and 4C are presently considered the most convenient and suitable for making devices according to an aspect of the invention, other fabrication methods will also work. According to an aspect of the invention, any fabrication method that results in a microchannel with apertures, made out of a material that supports electroosmotic flow is acceptable.

Each of FIGS. 4A, 4B and 4C shows a cross section of a device. Line 4-4 in FIG. 3 shows the section of device 310 that would be represented by FIG. 4A, 4B or 4C depending on which fabrication method is used to create the device. Regardless of the fabrication method used, the final result according to an aspect of the invention is a microchannel 100 with apertures 110 that connect the channel to a bath 480. Bath 480 is not shown in FIG. 4C because it is provided after layers 450 and 455 are removed during processing of the device.

FIG. 4A shows a cross section of a microfluidic channel device according to an aspect of the invention. The device is built starting from silicon wafer 410. Silicon nitride 405 is deposited on the wafer. Next standard lithography and etch techniques are used to create openings in the nitride on one side of the wafer. KOH, TMAH or another suitable etch is then used to etch through the silicon wafer until the nitride layer on the opposite side is reached. Apertures 110 are defined by lithography and then etched in the nitride layer. SU-8 photoresist 415 is spun on to the wafer and patterned to create the sidewalls of the microchannel. Finally the structure is bonded to PDMS layer 420.

FIG. 4B shows a cross section of a microfluidic channel device according to an aspect of the invention. The device illustrated in FIG. 4B has the advantage that PDMS layer 445 bonds well to nitride layer 440. The device is built starting from silicon wafer 430. Silicon nitride 425 is deposited on the wafer. Next standard lithography and etch techniques are used to create openings in the nitride on one side of the wafer. KOH, TMAH or another suitable etch is then used to etch through the silicon wafer until the nitride layer on the opposite side is reached. Apertures 110 are defined by lithography and then etched in the nitride layer. At this point polysilicon layer 435 is deposited and another nitride layer 440 is deposited on top of it. Openings are created in nitride layer 440 by standard techniques to expose regions in polysilicon layer 435 that will be etched away to form microchannels. Next polysilicon layer 435 is etched using a XeFl$_2$ etch or an anisotropic wet etch. Finally the structure is bonded to PDMS layer 445. The process just described in reference to FIG. 4B also works with the substitution of amorphous silicon for polysilicon for layer 435.

FIG. 4C shows a cross section of a microfluidic channel device according to another aspect of the invention. The device illustrated in FIG. 4C has the advantage that the final structure is flexible. Fabrication of this device starts with glass wafer 450 on which is deposited approximately 1500 Angstroms of amorphous silicon 455 on one side. Normally this is achieved by depositing amorphous silicon on both sides of the glass wafer and then removing it from one side. Apertures are defined and etched in amorphous silicon layer 455 using standard lithography techniques.

Next SU-8 photoresist 460 is spun on top of the amorphous silicon layer 455. In the figure, layers 455 and 460 are drawn as not touching. However, at this step layer 460 is in fact deposited on top of, and in contact with, layer 455. The layers are drawn separated to emphasize that later in the process glass wafer 450 will be released from the rest of the fabricated structure by etching away amorphous silicon layer 455.

SU-8 layer 460 is exposed through glass wafer 450 in a standard mask aligner or with a suitable light source. Since the light passes through glass wafer 450 before illuminating SU-8 layer 460, layer 455 acts as a photomask so that only the apertures defined earlier in layer 455 are transferred to layer 460. Development of exposed resist 460 is standard.

Layer 465 is then deposited. This layer could be polysilicon or a polymer such as SU-8, PMMA or polyimide. Next layer 470 is deposited as an adhesion layer between polysilicon or polymer layer 465 and PDMS layer 475. Layer 470 may be nitride, oxide or a polymer, for example. The next step is the bonding of PDMS layer 475 by standard techniques. Finally layers 465 and 470 are etched to form a microchannel. A XeFl$_2$ etch works well here since XeFl$_2$ etches through PDMS without disturbing it. Even though layer 475 covers layers 465 and 470, a XeFl$_2$ etch removes material in layers 465 and 470 without damaging PDMS layer 475.

Figure 5:
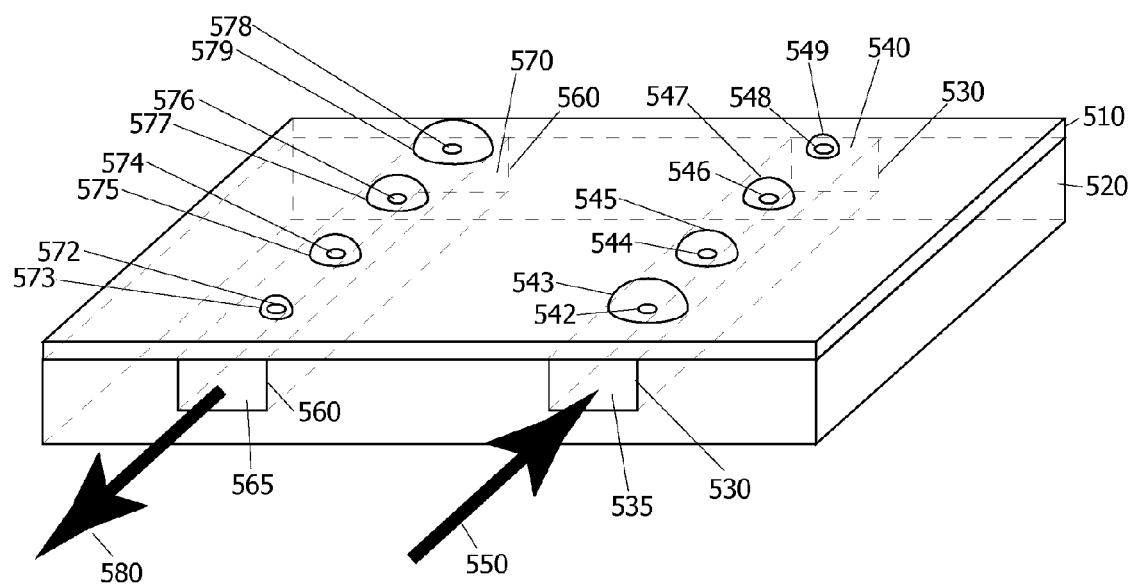
FIG. 5 shows a perspective view of a microfluidic channel device comprising more than one channel.

FIG. 5 shows a perspective view of a microfluidic channel device comprising more than one channel. In the device illustrated in FIG. 5 two microchannels 530 and 560 are shown. However, a device according to an aspect of the invention could comprise any number of microchannels or even interconnected networks of microchannels. Channels 530 and 560 are shown formed in a substrate layer 520 which is sealed by a cover layer 510. However, a microchannel device that is fabricated without a substrate and cover layer per se is acceptable according to an aspect of the invention. The main requirements on a microchannel device are that the materials from which it is fabricated support electroosmotic flow and that each channel has two or more apertures.

Each of the channels depicted in the device of FIG. 5 has four apertures in it. These are apertures 542, 544, 546, 548, 572, 574, 576, and 578. As mentioned before, however, each channel may have as few as two apertures or any number of apertures. An aspect of the invention includes devices in which each channel incorporates dozens, hundreds, or even thousands of apertures. The apertures connect the channels to a bath or reservoir of fluid. In FIG. 5 the device is designed such that all of the apertures are in contact with the same bath or reservoir. However, multiple, smaller reservoirs could be connected to groups of apertures instead of all of them. Each aperture must be covered by a bath or reservoir and each bath or reservoir must cover two or more apertures of a single channel.

Microchannels 530 and 560 have openings 535, 540, 565, and 570. These openings at the ends of the channels allow for inflow and outflow of fluid under the influence of electroosmotic flow, pressure, or both. In FIG. 5, electrodes, such as electrodes 115 of FIG. 1, are not illustrated; however, they are necessary to induce electroosmotic flow in the channels. For the sake of illustration, consider that electroosmotic flow has induced fluid flow from opening 535 toward opening 540 in channel 530 and from opening 570 toward opening 565 in channel 560.

If only electroosmotic forces were present, fluid would be ejected from some of the apertures of each channel and withdrawn into other apertures of each channel as discussed in reference to FIG. 1 above. However, in addition to the influence of electroosmotic forces, the influence of pressure is illustrated in FIG. 5. Consider that pressure has been applied to channel 530 at opening 535 as represented by in-flowing arrow 550 and also to channel 560 at opening 570 as represented by out-flowing arrow 580.

Pressure adds an overall bias to fluid flow through the apertures. In the case illustrated in FIG. 5, pressure has been applied in the same direction as the induced electroosmotic flow. This leads to fluid ejection from all apertures rather than ejection at some apertures and withdrawal at others. The fluid ejection is represented by schematic fluid boundaries 543, 545, 547, 549, 573, 575, 577, and 579. The relative size of the boundaries, decreasing in size from the high pressure end to the low pressure end of each channel, represents the amount of fluid ejected at each aperture.

The combination of electroosmosis and pressure in the device of FIG. 5 leads to the creation of micro gradients in the bath above the apertures in the device. These gradients are a new way to control concentration of molecular species in solution in a localized volume.

Figure 6:
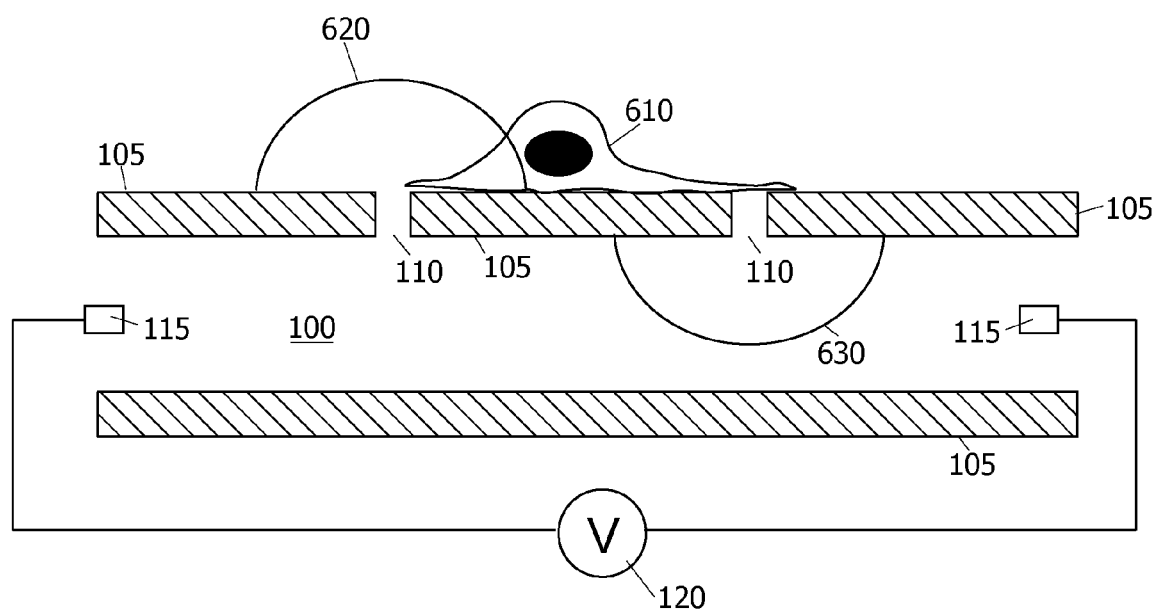
FIG. 6 shows a microfluidic channel device comprising two apertures in the channel.

FIG. 6 shows a microfluidic channel device comprising two apertures in the channel. The device works as described above in connection with FIGS. 1-5. In FIG. 6 only two apertures 110 are illustrated for clarity. However, devices with any number of apertures more than one are useful. FIG. 6 shows an application of a microfluidic channel device according to an aspect of the invention.

In FIG. 6 a biological cell 610 has been positioned in the bath near apertures 110 in a microfluidic channel device. The cell is near out-flowing and in-flowing fluid represented by schematic fluid boundaries 620 and 630. According to an aspect of the invention many novel investigations of the operation of cell 610 may be undertaken with the microfluidic channel device illustrated in FIG. 6. For example, tiny volumes of nutrients, stimulants, or other chemicals may be ejected near the cell as represented by schematic fluid boundary 620. Simultaneously, samples of the cells immediate microenvironment may be extracted from the bath as represented by schematic fluid boundary 630. These samples may be drawn through the microchannel for further analysis. Alternatively, experiments to determine if the cell is drawn toward an increased concentration of a chemical ejected from an aperture may be conducted.

In fact, any experiment involving changing or sampling the immediate microenvironment of a cell may be facilitated with a microchannel device according to an aspect of the invention. The cell is placed in a bath or reservoir near the apertures of a microchannel device and fluid is ejected, withdrawn or both from the channel under the influence of electroosmotic flow, pressure, or both.

FIGS. 7A, 7B, 7C and 7D show biological cells flowing into a microfluidic channel device. According to an aspect of the invention FIGS. 7A-7D show the operation of a microfluidic channel device in a cell positioning or cell sorting mode. Cells 740 flow inside microchannel 700 and arrange themselves near apertures 725. A cell positioning or sorting device as illustrated in FIGS. 7A-7D is useful for studies involving an ensemble of cells where individual cells must be monitored.

In FIGS. 7A-7D the walls of microchannel 700 support additional structures 720. Structures or blocks 720 serve to form indentations in the channel near apertures 725. These indentations are approximately sized so that a biological cell fits conveniently in them.

Cells 740 are introduced into microchannel 700 and flow along with a fluid filling the channel and the surrounding bath. Arrow 745 indicates the direction of fluid motion. The fluid in the channel flows under the influence of electroosmotic forces, pressure, or both as described in reference to FIG. 5. Cells in the channel are moved by the flowing fluid.

Figure 7A:
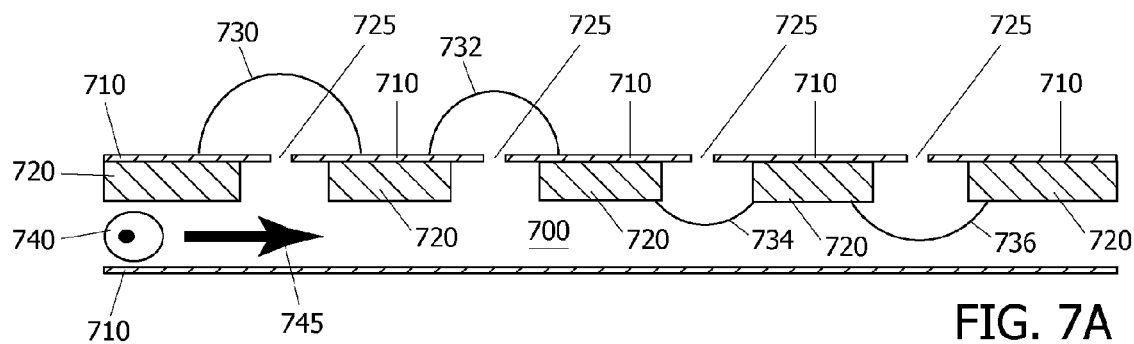
FIG. 7A, FIG. 7B, FIG. 7C and FIG. 7D show biological cells flowing into a microfluidic channel device.

An electric field is applied to microchannel 700 to induce electroosmotic flow along its length as indicated schematically by arrow 745. The field is applied by an electrical power supply and electrodes, omitted from the figure for clarity, but substantially the same as power supply 120 and electrodes 115 illustrated in FIGS. 1 and 6. As described previously electroosmotic flow along a channel with multiple apertures 725 to a bath leads to fluid out-flow and in-flow at apertures. In FIG. 7A fluid out-flow is indicated by schematic fluid flow boundaries 730 and 732 while in-flow is indicated by schematic fluid flow boundaries 734 and 736.

Figure 7B:
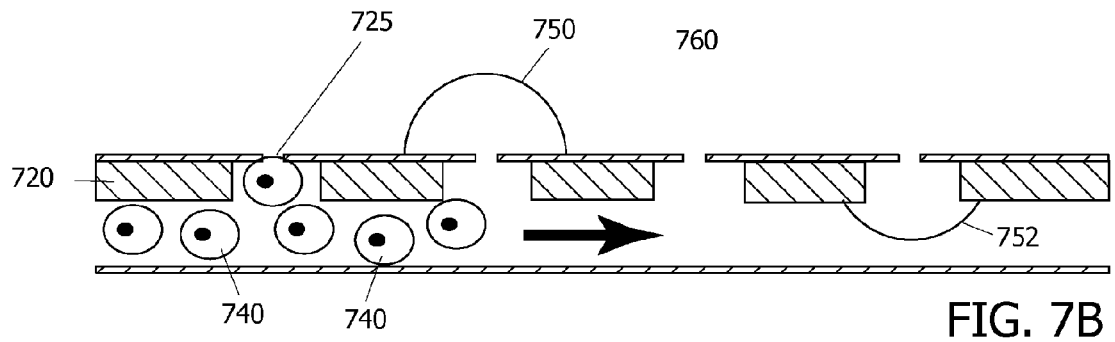

As cells 740 flow into the channel, some of them become lodged near apertures 725 between structures 720 as shown in FIG. 7B. When a cell blocks an aperture, fluid can no longer flow through that aperture and the electric field through the aperture is reduced to zero. In FIG. 7B a cell has blocked the first of four apertures. Comparing to FIG. 7A fluid out-flow 750 has increased compared to out-flow 732; fluid in-flow 734 has been reduced to zero; and fluid in-flow 752 is increased compared to in-flow 736. This new pattern of out-flow from, and in-flow to, the channel prepares the device to capture another cell at the second aperture.

Figure 7C:
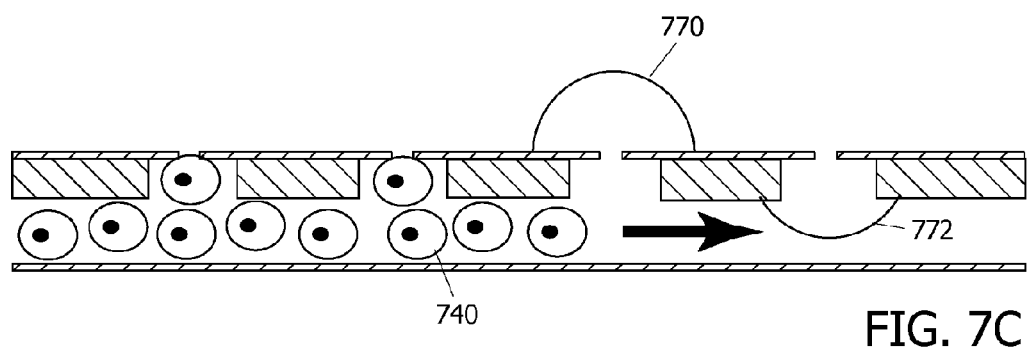

FIG. 7C illustrates the situation once cells have been captured at the first two apertures in the channel. Fluid out-flow 770 replaces the zero-flow situation 760 while in-flow 772 replaces in-flow 752. The device is ready to capture another cell near the aperture through which fluid flow creates out-flow zone 770. The process illustrated by FIGS. 7A-7C continues until only one open aperture is left in channel 700. This situation is illustrated in FIG. 7D.

Figure 7D:
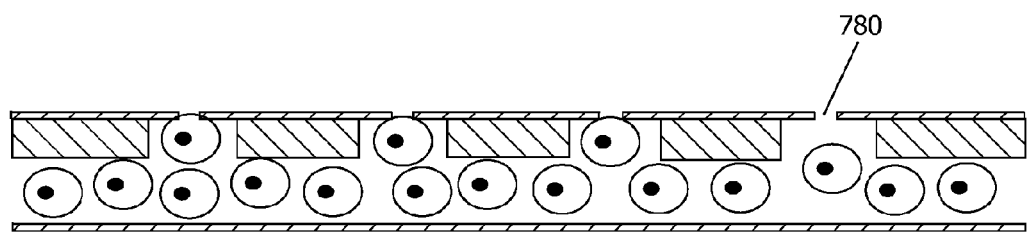

In FIG. 7D a channel has captured cells at all but one aperture. There is no electroosmotic force to capture a cell at the last open aperture because there is only a current path from the channel out of the aperture to the bath and no corresponding return path from the bath to the channel. However, cells in captured in all the other apertures will tend to remain in place; if they move away from the apertures, electroosmotic forces will tend to return them to their apertures.

Figure 8A:
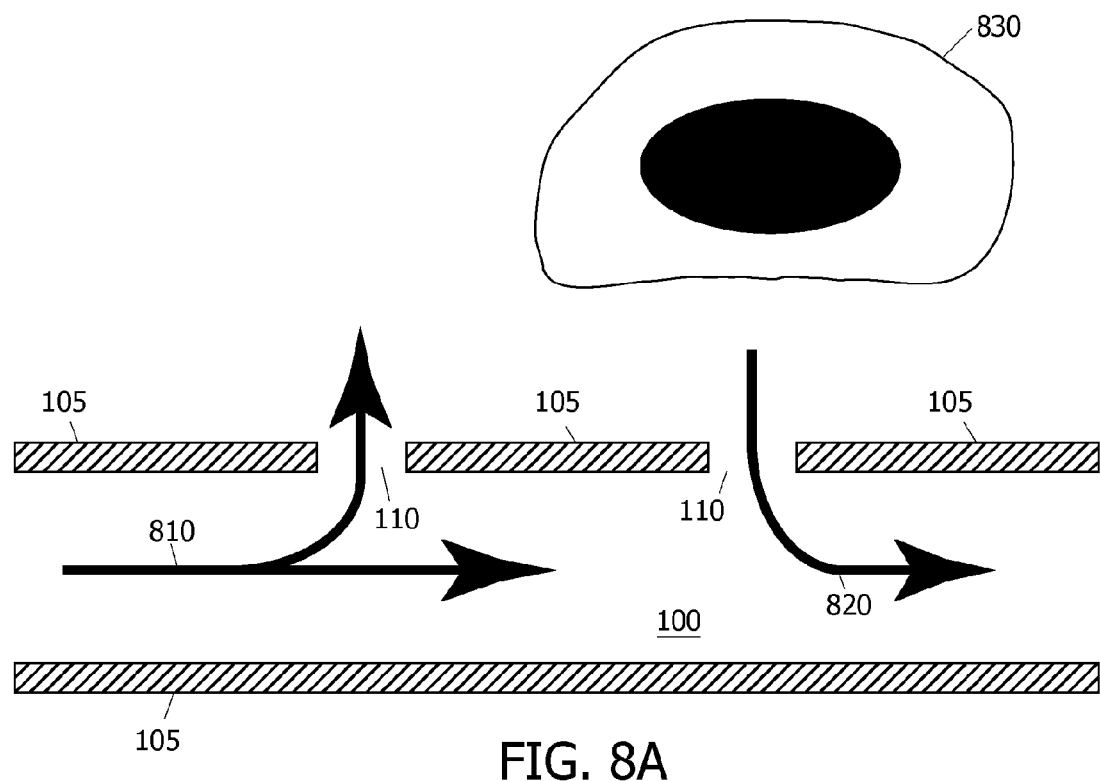
FIG. 8A and FIG. 8B show a biological cell interacting with a microfluidic channel device.
Figure 8B:
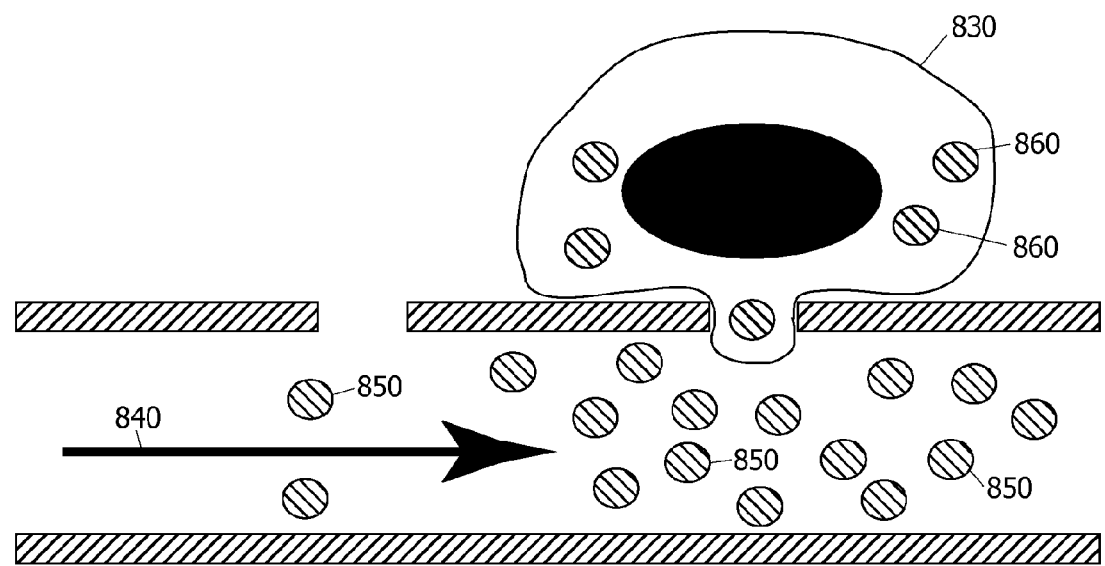

FIGS. 8A and 8B show a biological cell interacting with a microfluidic channel device. The cell is drawn from the bath toward an aperture of the device and held in place in the aperture by forces of electroosmotic flow. Biological agents 850 are introduced into the channel and inserted into cell 830. The agents penetrate the cell membrane and act within the cell.

FIG. 8A illustrates a microchannel device similar to that described in reference to FIGS. 1, 5, and 6. Arrows 810 and 820 indicate the direction of fluid flow under the influence of electroosmotic forces which are the result of an applied electric field along the length of the channel. The electric field may be applied with a voltage source and electrodes as previously discussed.

Biological cell 830 is drawn toward an aperture where fluid is flowing from the bath into the channel. Depending upon the relative size of the cell and the aperture, the type of cell, and the surface chemistry of the aperture, the cell may be somewhat drawn into the aperture as shown in FIG. 8B. Once the cell is in position, biological agents 850 are introduced into channel 100. Biological agents may be, for example, fluorescent dyes, quantum dots, or other labels. Alternatively biological agents may be proteins, enzymes, or chemical species. The flow of biological agents is predominantly straight down the channel as illustrated by arrow 840. There is little flow out of the open aperture since it is a single aperture with no available return path for electric current. Biological agents 850 are then in position to insert themselves into cell 830 as shown by agents 860. Agents 860 have crossed the cell membrane and now influence the interior of the cell.

According to an aspect of the invention, the device illustrated in FIGS. 8A and 8B is useful for studies involving exposing cells to biological agents or inserting such agent into living cells in a controlled manner.

Figure 9A:
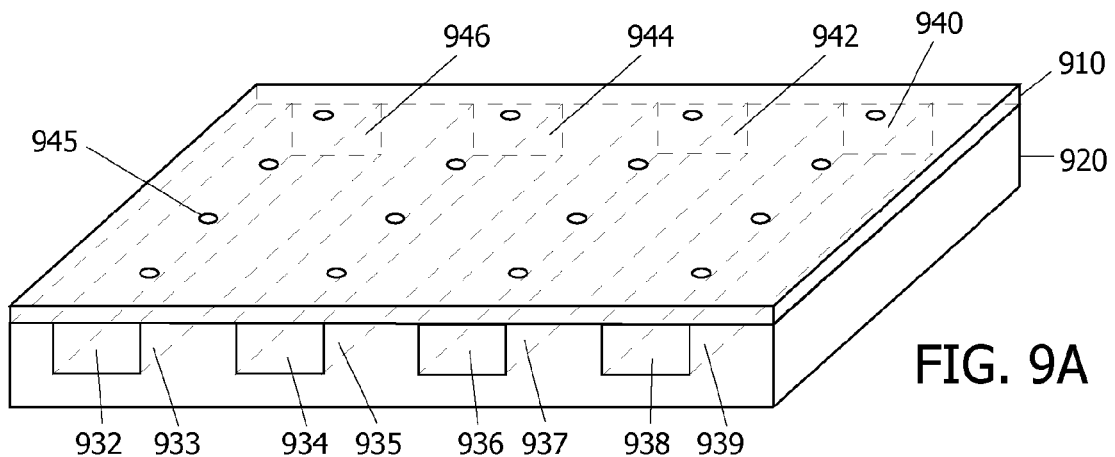
FIG. 9A, FIG. 9B and FIG. 9C show a microfluidic channel device comprising multiple channels.
Figure 9B:
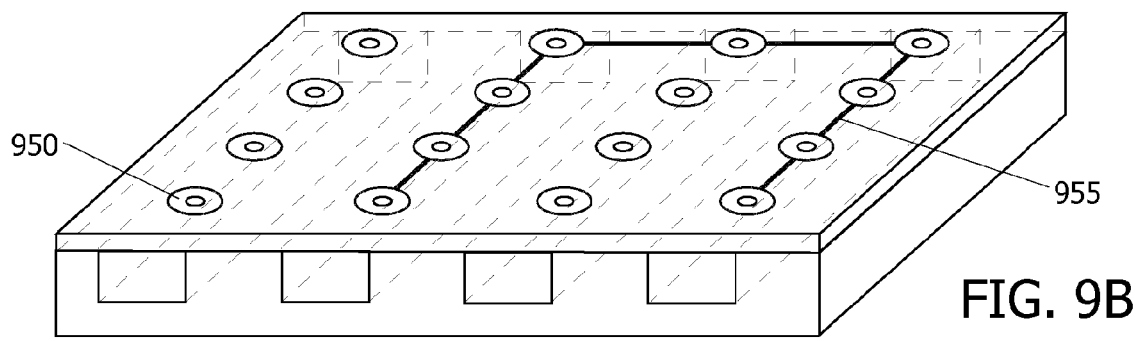
Figure 9C:
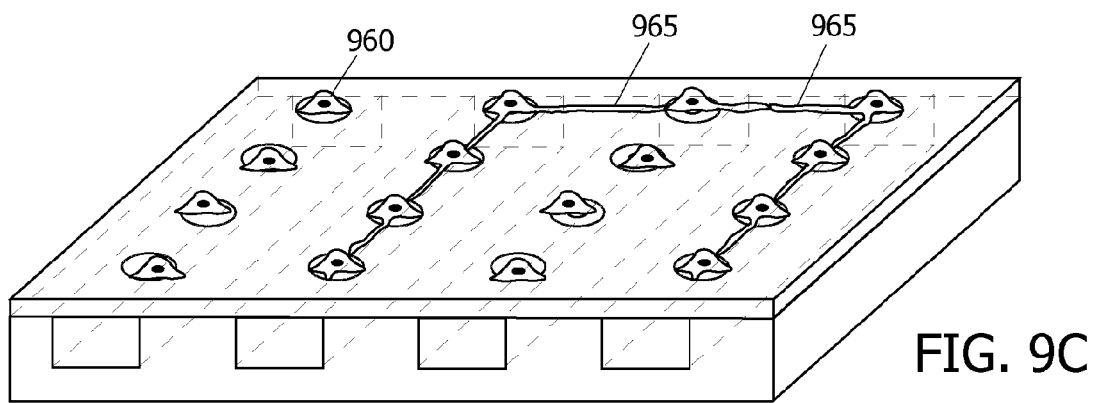

FIGS. 9A-9C show a microfluidic channel device comprising multiple channels. Four channels are illustrated; however, a device according to an aspect of the invention may have any number of channels. In addition to having multiple channels, the device of FIGS. 9A-9C is modified by the application of surface chemical agents. These agents could include adhesion proteins or other chemical or biological species that modify the surface of the device and affect its interaction with living cells. Surface modification of a microchannel fluidic device enhances its properties by promoting cell adhesion to specific parts of the device and even promoting cell growth in specific surface regions of the device.

FIG. 9A shows a four-channel microfluidic channel device according to an aspect of the invention. The device as drawn is composed of a substrate 920 into which channels 933, 935, 937, and 939 are etched. Each channel has openings at its ends such as openings 932, 934, 936, 938, 940, 942, 944, and 946. Furthermore each channel has two or more apertures, such as aperture 945, which connect the channel to a bath.

In order to promote cell adhesion and growth on specific areas of the device, adhesion molecules or proteins are patterned on the device surface. For example in FIG. 9B regions, such as region 950, are coated with cell adhesion promoters and connecting regions, such as connecting region 955, are coated with cell adhesion and growth promoters. When cells are introduced to the bath in contact with the device they will tend to stick to the surface of the device in locations where cell adhesion promoters have been deposited. This is illustrated in FIG. 9C. Cells, such as cell 960, tend to stick to the device near apertures since that is where adhesion promoter 950 has been placed. Further, cells will grow dendrites or protrusions 965 along the connecting regions 955 where cell adhesion and growth promoters have been placed.

According to an aspect of the invention FIGS. 9A-9C show a new way to make an interface between man-made microfluidic devices and living cells. The cells grow on the device in specific locations according to the pattern of adhesion promoters and are addressed by fluid solutions in microchannels within the device. Solutions in the microchannels are brought into contact with the living cells through apertures in the channels.

While the invention has been described in connection with what are presently considered to be the most practical and preferred embodiments, it is to be understood that the invention is not limited to the disclosed embodiments and alternatives as set forth above, but on the contrary is intended to cover various modifications and equivalent arrangements included within the scope of the following claims.

As one skilled in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps. Therefore, persons of ordinary skill in this field are to understand that all such equivalent arrangements and modifications are to be included within the scope of the following claims.

What is claimed is:

1. A device for creating microgradients in solution comprising:
    a microfluidic channel with openings at each end and two or more apertures in the channel walls;
    two and only two electrodes: a first electrode placed in or near a first opening at a first end of the channel, and a second electrode placed in or near a second opening at a second end of the channel; and,
    an electrical power supply connected to the electrodes; wherein,
    the apertures are continuously in contact with an external fluid bath while the openings are isolated from the bath.

2. A device as in claim 1 wherein the power supply is connected to the electrodes such that several distinct current paths exist from one end of the channel to the other and current flows along all of these paths when an electric field is applied along the channel by the combination of the power supply and the electrodes.

3. A device as in claim 1 wherein the power supply is connected to the electrodes such that simultaneous flow of fluid occurs through two or more of the apertures and a chemical concentration gradient is formed near the apertures.

4. A device as in claim 1 wherein the length of the channel is between about ten microns and ten millimeters, the transverse dimension of the channel is between about 0.1 and one hundred microns, and the dimensions of the apertures are between about 0.1 and ten microns across.

5. A device as in claim 1 further comprising structures that form indentations in the channel near the apertures, such indentations being approximately the size of a living cell.

6. A microfluidic device comprising:
    a microfluidic channel defining a flow path for a fluid having a known concentration of a selected chemical, the microfluidic channel comprising a plurality of apertures defined in the channel for providing continuous fluid communication between the channel and a reservoir containing a sample solution, and an inlet and an outlet that are isolated from the reservoir;
    electric field means provided for inducing electroosmotic flow along the flow path, wherein the electric field means comprise a number of electrodes that is less than or equal to the number of apertures; and,
    means for applying pressure to the fluid in the flow path such that fluid flows simultaneously out of the channel at the apertures and forms a concentration gradient at the apertures along the channel such that cells cultured near each aperture are exposed to a separate concentration of the chemical corresponding to the location of the aperture along the concentration gradient.

* * * * *